United States Patent [19]

Doane

[11] Patent Number: 4,747,683

[45] Date of Patent: May 31, 1988

[54] METHOD AND DEVICE FOR IN VIVO WETTING DETERMINATIONS

[75] Inventor: Marshall G. Doane, Cambridge, Mass.

[73] Assignee: Eye Research Institute of Retina Foundation, Boston, Mass.

[21] Appl. No.: 820,526

[22] Filed: Jan. 17, 1986

[51] Int. Cl.[4] .......................... G02C 7/04; A61B 3/00; A61B 3/10; A61B 3/14

[52] U.S. Cl. .................................... 351/206; 351/221; 351/205; 351/177; 351/219; 351/247

[58] Field of Search ............... 351/247, 205, 206, 219, 351/211, 221, 160 R, 160 H, 177, 246; 356/357; 128/664, 665, 633; 354/62

[56] References Cited

U.S. PATENT DOCUMENTS

| | | | |
|---|---|---|---|
| 3,816,649 | 6/1974 | Butters et al. | 356/357 |
| 3,943,278 | 3/1976 | Ramsey, Jr. | 356/357 |
| 4,221,486 | 9/1980 | Jaerisch et al. | |
| 4,256,384 | 3/1981 | Kani et al. | 351/206 |
| 4,266,861 | 5/1981 | Sawa | 351/206 |
| 4,377,343 | 3/1983 | Monson | |
| 4,443,106 | 4/1984 | Yasuda et al. | |
| 4,453,828 | 6/1984 | Hershel et al. | |
| 4,500,615 | 2/1985 | Iwai | |
| 4,653,922 | 3/1987 | Jarisch et al. | 356/357 |

FOREIGN PATENT DOCUMENTS 0167877 1/1986 European Pat. Off. .

OTHER PUBLICATIONS

International Tear Film Symposium—1984—Program and Abstracts, Nov. 7–10, 1984, Lubbock, Texas, p. 71.
7th Montreal International Symposium on Contact Lenses, Oct. 12–13, 1985, Abstract of Jean-Pierre Guillon.
Tear Film Structure and Contact Lenses, J. P. Guillon in The Preocular Tear Film, F. J. Holly, ed., Lubbock, Tx 1986.

Primary Examiner—Rodney B. Bovernick
Assistant Examiner—Jay Ryan
Attorney, Agent, or Firm—Lahive & Cockfield

[57] ABSTRACT

A method for evaluating the in vivo ability of a contact lens to become or remain wet includes the steps of supporting the subject's head to determine a fixed orientation of the lens, illuminating the lens with coherent light, imaging the pre-lens tear film in a manner to form an interference pattern, recording in a time sequence manner the image formed thereby, and determining the tear film thickness by correlating the interference bands of the recorded image. The classical contact angle is derived, and other measures, such as the time interval from blink until the onset of the tear film breakup, or the time until the film evaporates, and the initial or average film thickness are derived. In addition, the nature and evolution of localized dry spots may be directly observed, clarifying the causes of tear film breakdown on worn contact lenses. The invention includes methods for the evaluation of wetting characteristics as they are affected by lens material, lens aging and lens soiling, as well as the evaluation of solvents, additives and cleaners, for their effects on wetting characteristics.

Apparatus for performing the method include a means for supporting the head so as to determine a fixed location of the contact lens, a coherent light source, and a camera focused at the pre-lens film from a position to image light from the source specularly reflected from the front and rear surfaces of the tear film. A film motion analyzer provides numerical coordinates of interference bands, and a microprocessor analyses the coordinates to provide a quantitative measure of lens position or wetting characteristics.

16 Claims, 3 Drawing Sheets

METHOD AND DEVICE FOR IN VIVO WETTING DETERMINATIONS

BACKGROUND OF THE INVENTION

This invention relates to the testing and evaluation of eye wetting, and more particularly to the wetting of contact lenses worn on the eye of a subject.

It is commonly assumed that the wettability of a contact lens is directly related to its comfort, optical qualities, and wearing qualities. The bare eye is normally protected by a tear film having a thickness in the range of 6–7 microns. This tear film is composed primarily of an aqueous saline solution, with lesser components of lipid and of mucin, an assortment of glycoproteins. The fluid also contains debris, such as dust and sloughed epithelial cells. The normal precorneal tear film on the bare eye is quite stable. The aqueous component may be calculated to thin out to the point of break-up by pure evaporative processes over a time interval of 5–10 minutes. The film is refreshed upon blinking, and the normal interblink interval is substantially shorter than 5 minutes, so drying-out is not normally encountered.

By contrast, when a contact lens is placed on the eye, each blink of the lid refreshes a tear film on the outer surface of the contact lens, called the prelens tear film, which is typically less than 1 micron in thickness. Drying of the film to zero thickness typically occurs in under 10 seconds. A dry lens can be uncomfortable sticks to the eye and lids, and may be expected to display inferior optical performance due to scattering from uncovered surface imperfections. In addition, a lens which has been subject to repeated drying cycles is likely to have permanent solid deposits built up thereon, which accelerate subsequent tear film breakup and promote trauma or infection.

For these reasons, "wettability" of contact lenses is deemed desirable. Various wetting traits have been taken by the industry as measures of wettability. A common measure of wettability is the "contact angle" determined by the angle of the tangential plane of the edge of a fluid drop with the plane of the lens surface where they meet. This measurement is generally made at a clean interface of a solid with a given fluid, and the measurement must be performed with some delicacy. It is not clear how a contact angle measurement performed under laboratory conditions correlates with the contact angle of tear fluid on an in vivo contact lens in which the lens has been repeatedly exposed to mucins, lipids and other tear film components. One researcher has reported making in vivo contact angle measurements using drops of distilled water placed on the lens. Applicant is not aware of in vivo contact angle measurements using actual tear fluid.

Other approaches to determining in vivo wettability might involve adding a dye, such as fluorescein, to the tear fluid to visualize the thin prelens tear film. However it is desirable to develop a method or apparatus to measure lens wettability which directly measures the thickness and distribution of the prelens tear film, and which does not introduce extraneous substances, such as dyes or fluids which might alter the measurements.

Accordingly, there is a need for a method and apparatus for directly determining the wettability of a contact lens in a manner which meaningfully relates to the environment in which the lenses are used.

SUMMARY AND OBJECT OF THE INVENTION

It is an object of the invention to provide a method for evaluating the in vivo ability of a contact lens worn by a subject to become or remain wet.

It is another object of the invention to provide a method for evaluating the wettability in vivo of different contact lens materials.

It is another object of the invention to provide a method of evaluating the effect on wettability of different lens cleaners or eye treatment fluids.

It is another object of the invention to provide a method for evaluating the effects of use or age on the wettability of a contact lens.

It is another object of the invention to provide a device for performing one or more of the above methods.

These and other objects of the invention are obtained in a method for evaluating the in vivo ability of a contact lens to become or remain wet, in which the method includes the steps of supporting the subject's head to determine a fixed location of the lens, illuminating the lens with coherent light, imaging the pre-lens tear film in a manner to form an interference pattern, recording in a time sequence manner the image formed thereby, and determining the tear film thickness by correlating the interference bands of the recorded image. The spacing of adjacent bands gives a measure of the tear film thickness distribution from which the classical contact angle may be derived. Other measures, such as the time interval from blink until the onset of tear film breakup, or the time until the film evaporates may be determined, and the initial or average film thickness may be derived. In addition, the nature and evolution of localized dry spots may be directly observed, clarifying the causes of tear film breakdown on contact lenses. The invention also contemplates a method for the evaluation of wetting characteristics as they are affected by lens material, lens aging and lens soiling, as well as the evaluation of solvents, additives and cleaners, for their effects on wetting characteristics.

An apparatus for performing the method include a means for supporting the head so as to determine a fixed location of the contact lens, a coherent light source, and a camera focused on the pre-lens film from a position that images the light from the source that is specularly reflected from the front and rear surfaces of the tear film. A film motion analyzer is used to quickly obtain the location and separation of interference bands. A microprocessor computes the tear film thickness at each band location, and provides a quantitative measure of lens wetting characteristics.

BRIEF DESCRIPTION OF THE DRAWINGS

These and other features will be understood with reference to the figures, in which.

DETAILED DESCRIPTION

The present invention provides a method and apparatus for directly measuring the thickness of the prelens tear film distributed over the surface of a contact lens and changing over the course of time. The invention further contemplates measuring the layer as it is affected by solvents, cleaners, treatment fluids, lens materials, and different environmental or use factors which affect the lens worn by the user. As applied to the method of the invention, the evaluation of such solvents, components, or conditions are included under the general term "wettability" or "wetting characteristics", and accordingly as used in this disclosure and the claims below it is the intention to describe and claim the clinical or laboratory practice of the methods and device of the invention for evaluating all such solvents, lenses, products and conditions affecting the wetting of a contact lens.

Figure 1:
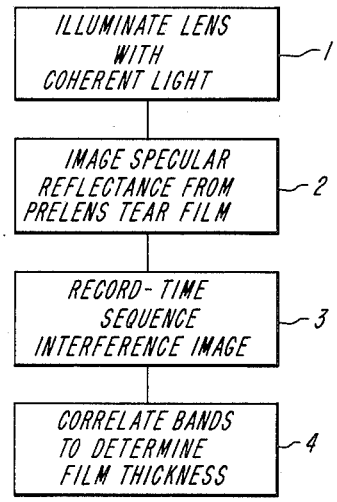
FIG. 1 is a block diagram of the steps involved in the method according the present invention.

Returning now to FIG. 1 the method of the invention includes the steps of (1) illuminating the lens with coherent light; (2) forming an image of the prelens tear film by the light specularly reflected from the pre-lens tear film; (3) recording the image including the interference patterns therein, in a time sequence manner; and (4) determining the thickness of the prelens tear film by correlating bands of the recorded interference patterns.

It will be appreciated as a general matter, that when light is specularly reflected from the front and rear surfaces of a sufficiently thin film, the images of the reflected light will form interference patterns because the variable thickness of the film is such that the front and rear reflected light rays interfere constructively or destructively at different positions. In general, to provide a meaningful interference pattern, a film must have a thickness in the range of approximately ¼ to several whole wavelengths of the incident light, and must exist in an environment in which sufficient specular reflections from its upper and lower surfaces occur. As an aid to understanding the value of the method used to visualize the dynamic spreading, thinning and breakup of the prelens tear film, basic principles of interference phenomena will now be discussed in relation to FIG. 2. Further details of the optical theory may be found in optical textbooks.

The changing colors of a soap bubble, or of a thin film of oil floating on water, are each common manifestations of light interference. This phenomenon is observed when two or more beams of light from a common source arrive along different paths at the same region of space. In each of the two cases mentioned above, the interfering beams are those reflected at the two surfaces of a thin film. In the first case the film is a film of soapy water in air; in the second case it is a film of oil between air and water. Under the proper conditions, similar interference colors, or bands, can be reflected from the tear film on the surface of the cornea or a contact lens. As described below, in accordance with the present invention, such interference patterns are formed and recorded to give precise and detailed information of the topography of the tear (or lipid) layer overlying the cornea or a contact lens.

The invention is best understood after a brief discussion of interference phenomona, modeled using the wave model of light. In general a light wave is a transverse electromagnetic disturbance propagated through space. When two or more light waves cross a point, the amplitude of the disturbance at that point is the superposition of the amplitudes of the individual waves. This superposition principle follows from the linear character of Maxwell's equations. Generally, the superposition of several light waves does not produce an interference pattern. This is because most light sources used for observations consist of a large number of microscopic, uncorrelated sources, each of which is active for certain short periods of time and quiescent the rest of the time. Assuming, for the sake of argument, that during their active periods all of the sources emit trains of sinusoidal waves of the same wavelength, the resultant optical disturbance produced by the source as a whole would be represented as a sinusoidal function of time, whose phase and amplitude change whenever one of the sources goes on or off. Thus the optical disturbances produced by two such microscopic sources, however similar they may be, will have a phase difference that varies rapidly and irregularly with time. Such a source is said to be incoherent. The positions of the interference fringes will change as the phase difference changes. At a given instant the maximum intensity will occur at a point where a minimum was present only a short time before, and vice versa. Since most optical instruments cannot resolve such rapid and irregular fluctuations of intensity, the observable result will be a uniform illumination. In order to observe interference phenomena, it is necessary to use coherent light sources, that is, sources whose phase difference remains constant in time. The only manner in which this can be practically accomplished is to use a single light source and its optical image, or to use two different images of the same source.

According to the present invention, interference patterns are created by using two images of the same source. Specifically two interfering beams are used: the reflected beam from the front surface of the tear film and the reflected beam from the rear surface of the tear film. The two beams originate from the same single light source, and in fact are two images of it, so the beams satisfy the requirements of coherence. To observe specular reflectance, the angle the incoming beam makes with respect to a direction perpendicular to the tear film surface must equal the angle of observation. This is usually stated as "the angle of incidence equals the angle of reflection." Any light seen at other angles is due to light scattering from the surface, and such light does not maintain its uniform phase relationships with the incoming beam; thus interference bands are not seen.

Figure 2:
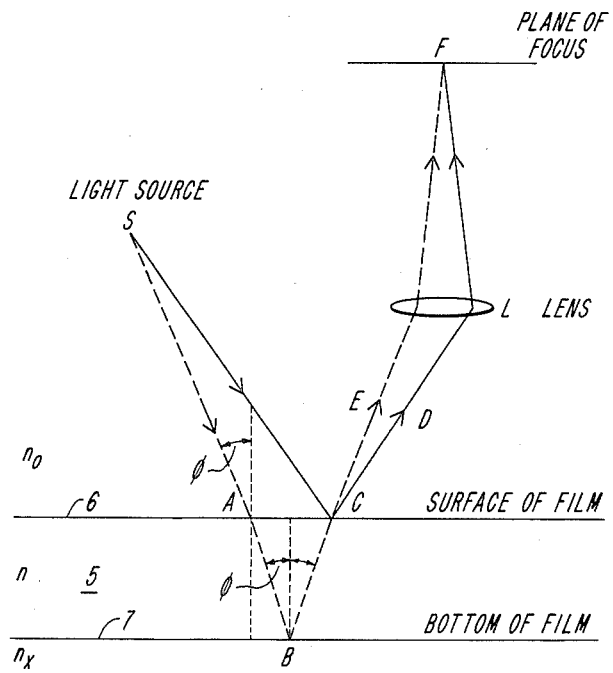
FIG. 2 is a diagram showing the theory of interference band measurements.

FIG. 2 is a diagram of a representative film 5 having front and rear surfaces 6, 7 and illuminated by a source S. Light from source S falls on the film 5, such as the tear layer, and light rays are reflected by the film to a converging lens L which forms an image of the film on a focal plane F. Consider the ray SCD reflected from point C at the upper surface of the film. Another ray SABCE passes through the same point C after having been reflected at point B of the lower film surface. The lens L brings the two rays together again at point F which forms an image of point C. To determine the phase difference, note that the optical path lengths of the two rays from S to C are $p_1 = n_0 SC$, and $$p_2 = n_0 SA + n(AB + BC)$$

where n is the refractive index of the film and $n_0$ that of the medium through which the incident light ray is travelling ($n_0 = 1$ if this medium is air). Therefore $$p_2 - p_1 = -n_0(SC - SA) + n(AB + BC).$$

Let t be the thickness of the film, and $\phi$ and $\phi'$ the angles of incidence and refraction of the ray SA. According to Snell's law for refraction at interfaces of different refractive index $n_0 \sin \phi = n \sin \phi'$. Considering that the film is very thin, CA is very small compared with SA, and we obtain, to a good approximation, $$\begin{aligned} n_0(SC - SA) &= n_0 CA \sin\phi \\ &= 2tn_0 \tan\phi' \sin\phi \\ &= 2tn(\sin^2\phi'/\cos\phi') \text{ and} \\ n(AB + BC) &= 2tn/\cos\phi'. \end{aligned}$$

Therefore, $$p_2 - p_1 = 2tn(-\sin^2\phi'/\cos\phi' + 1/\cos\phi') = 2tn \cos\phi'.$$

The phase difference corresponding to this difference in optical path length is $2(\pi)(p_2 - p_1)/\lambda_0$ where $\lambda_0$ is the wavelength in vacuum (or air, in practical terms). There is, however, an additional phase factor to consider. When a light ray is reflected from a surface such that the ray is incident from a media of lower refractive index than the substrate reflecting media, the situation is just as described above. However, if the incident ray is travelling in a media of higher refractive index than the reflecting surface, there is a phase change of 180 degrees, or $\pi$ radians, between the incident ray and its reflection. The ray SCD is reflected at the upper surface of the film, where the index of refraction changes from $n_0$ to n, and since $n_0$ is less than n (i.e., the refractive index of air is essentially 1.0, while that of the tear film is similar to that of water, where n=1.33), there is no phase change for the reflected ray. The ray SABCE is reflected at the lower surface, where the index of refraction changes from n to $n_x$, where $n_x$ is the refractive index of the medium beneath the film layer. If $n_x$ is less than n, there will be a change of phase of $\pi$ upon reflectance; if $n_x$ is greater than n, the case will be as with the surface ray, and no phase change will occur. In the case where we are dealing with a tear film layer (n=1.33) on a contact lens, the lens will always have a higher value (for $n_x$) than 1.33. If the lens is PMMA, $n_x$ will be about 1.49; if the lens is a hydrogel, it will be less, but will still be at least slightly greater than the tear film, so no phase change need be considered.

Thus, the two reflected rays meet at C and then again at F with a phase difference $\alpha$ given by $$\alpha = 2\pi(p_2 - p_1)/\lambda_0, \text{ or}$$

$$\alpha = 2\pi(2tn \cos\phi')/\lambda_0$$

In particular, if the lens is so located as to collect rays that are reflected by the film in a nearly perpendicular direction, $\cos \phi'$ is very close to unity, and the above equation reduces to $$\alpha = 2\pi(2tn/\lambda_0).$$

Interference of the two rays at F produces a maximum of intensity if $\alpha$ is an odd multiple of $2\pi$, that is, if the condition $$2tn/\lambda_0 = k,$$

$k = 0, 1, 2, \ldots$ is satisfied. The interference will produce a minimum of intensity if $\alpha$ is an even multiple of $\pi$, that is, if $$2tn/\lambda = k + \tfrac{1}{2},$$

$k = 0, 1, 2, \ldots$

If we let $\lambda = \lambda_0/n$ be the wavelength in the film, we can rewrite these equations as

| | |
|---|---|
| Interference maxima: $t = k(\lambda/2)$ | Equation (A) |
| Interference minima: $t = (2k+1)\lambda/4$ | Equation (B) |

From this we can conclude that the interference maxima occur where the tear film thickness t is an even multiple of $\lambda/4$, and minima (dark bands) occur where the tear film thickness t is an odd multiple of $\lambda/4$.

With a tear film of varying thickness over the field of view, which is illuminated with a monochromatic light source, a pattern of light and dark bands, or interference fringes, will be seen. The lines where the thickness of the tear film satisfy Equation (A) will stand out as lines of maximum brightness, and those where the thickness of the film satisfy Equation (B) will appear as dark lines.

Using a point source of light as illumination, interference fringes are seen only on that portion of the tear film that reflects the light rays from the source into the observing (collecting) lens. This portion becomes smaller as the diameter of the observing lens decreases. However, if the diameter of the observing lens is sufficiently small compared with the distance of the lens from the surface of the tear film one can use a broad source of light and observe interference patterns from a wider portion of the tear film. This is because with a small observing lens diameter, the angle of reflection $\phi'$ is practically the same for all rays reflected at a given point of the tear film into the lens, and so, for all pairs or rays that can enter the lens (L of FIG. 2) $\cos \phi'$ and t are constant and the phase difference $\alpha$ also has a constant value.

The "ideal" case shown in FIG. 2 represents a plane for the reflecting surfaces. In the case of a contact lens, the surfaces are, of course, sharply curved. This limits the angles of reflected rays that are collected by the observing lens, so the field of view over which the interference patterns are seen are much less than if plane surfaces were involved. Nevertheless, by optimal use and placement of the light source, subject, and collecting lens, a field diameter of at least 4 to 5 mm can be observed at one time. This seems to be adequate for evaluating the general characteristics and dynamics of the tear film as it exists on the surface of the contact lens.

Figure 3:
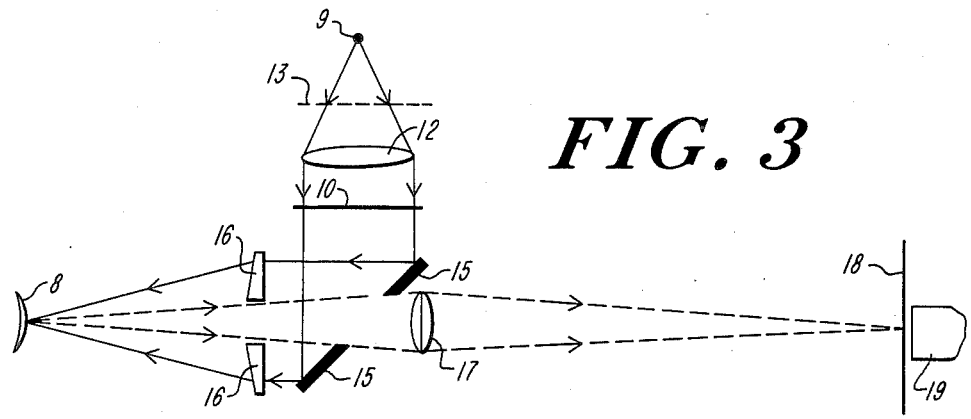
FIG. 3 is a schematic representation of the optical apparatus of a preferred embodiment of a device according to the invention for performing the method of FIG. 1.

FIG. 3 shows a schematic optical set-up for observing interference fringes in the tear film on a contact lens. This arrangement permits the illumination and observation of the tear film to be performed essentially along an axis orthogonal to the lens and aligned with the optical axis of the eye. In this arrangement, the interference fringes remain sharp over a large area of the contact lens since cos φ changes quite slowly over the surface of the lens in the region where φ equals 0, that is when the incident light is nearly coaxial with the center of curvature of a contact lens radius line.

A prototype instrument according to FIG. 3 was built using the optics from a conventional keratometer, suitably modified. In this device a light source 9 and collimating lens 12 direct light onto a translucent diffusion screen 10. The image of screen 10 is reflected by mirror 15 having a central aperture to a converging lens 16 which directs the light in a cone onto contact lens 8. In this manner, contact lens 8 is illuminated essentially along its central axis. Light reflected from the lens travels back, essentially along the axis, through the aperture of mirror 15 and is focused by lens 17 onto an image plane 18. In one embodiment, the light source 9 was a conventional photographic 35 mm slide projector. Heat absorbing glass was used to remove the infrared light, and a narrow band filter 13 (shown in phantom) having a half band width of approximately 20 nm and centered at 500 nm was used to provide a source of known wavelength. The condensing lens 16 and the focusing lens 17 were chosen to provide a working distance of approximately 4 to 6 inches between the instrument and the contact lens. Lens 17 had a focal length of approximately 4 inches, a numerical aperture of approximately f/4, and was set up at approximately a 1:1 image to object ratio. The focal plane 18 was aligned with the focal plane of a motion picture camera spaced approximately fifteen inches from the eye. The apparatus of FIG. 3 is representative, and variations in the design are possible.

It will be observed that with the device in FIG. 3 having a diffuse light source, rays originating from different points of the source will generally form interference patterns which do not overlap. The result is an essentially uniform level of illumination across the plane of observation. However, if the source is not too extended and if the rays from the source strike the tear film in directions not too far from the perpendicular to the surface of the tear film, then in the plane of the tear film itself the various systems of interference fringes are almost exactly coincident. This will not happen in any other plane except the plane on which the converging lens 17 forms a real image of the tear film. The interference fringes produced by the variable thickness of the tear film under these conditions are said to be localized in the plane of the tear film. By placing camera 19 at the focal plane 18, a picture of the interference pattern representative of tear film thickness is obtained.

It is not necessary that the light source be a diffuse source. One may, for example, use a laser light source, with an appropriate scanning mechanism, such as a rotating polygonal mirror. When scanning with such a source one must be careful to arrange the scanning optics so as to avoid "burning" caused by the eye focusing the scanning laser at a fixed interior point, e.g. on the fundus. When using a laser it is also desirable to use a beam expander to provide a beam of coherent light of sufficient diameter. Neither is it necessary that the light source be used in connection with the apertured mirror observation system illustrated in FIG. 3.

Figure 4:
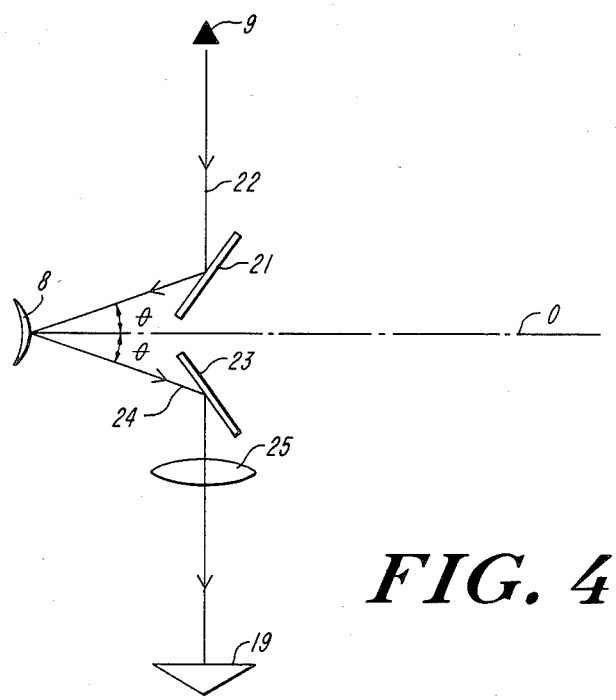
FIG. 4 shows an alternative layout of optical elements of another device according to the invention.

An alternate arrangement of optical elements for recording interference patterns formed by the prelens tear film is shown in FIG. 4. This arrangement includes a first mirror 21 directing the coherent light beam 22 from source 9 to the contact lens, and a second mirror 23 placed on the opposing side of the central axis "0" for receiving the image 24 specularly reflected from the tear film and directing it to a focussing lens 25 so as to form an interference pattern in the film plane of camera 19. The two-mirror arrangement permits illumination and imaging of the film at the same angle from the central axis, chosen to be small. Other arrangements will occur to those skilled in the art. For instance, the angles of the mirrors can be changed or even rapidly tilted to allow a larger area of the lens surface to be observed. For such a device, when the source light mirror directs the beam at a point x on the lens at an angle φ with respect to the normal N at that point, the receiving light mirror 3 should be tilted to receive light reflected at such angle φ. By providing mechanics for causing mirrors 21, 23 to rotate in synchrony in this manner, a larger portion of the lens may be imaged.

Figure 5:
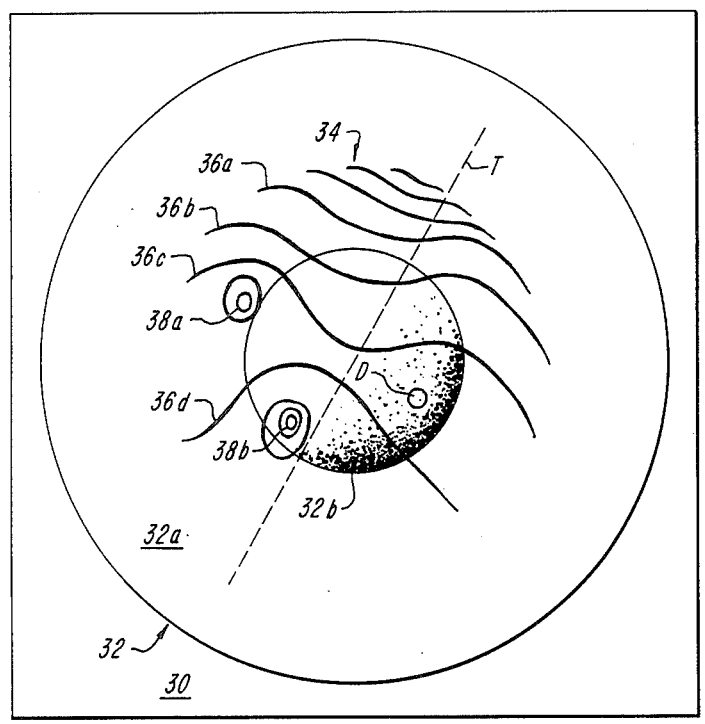
FIG. 5 shows a representative image of the pre-lens tear film and interference patterns recorded in accordance with the invention.

FIG. 5 shows an example of the image 30 formed by lens L (17 of FIG. 3, or 25 of FIG. 4) and recorded by the camera 19 as a single frame. A representative image includes a diffuse, or unfocussed image 32 including cornea 32a of the subject's eye, and a sharper image 34 of the pre-lens tear film. A central dark region 32b results from the geometry of the light source and imaging optics of FIG. 3. The image of the pre-lens tear film includes an interference band pattern 36a, 36b, etc., and also includes in sharply delineated focus, such opaque physical debris as may be present in the tear film. The dark interference bands 36a . . . each lie along a contour of equal depth of the tear film, and are formed at those contours where the depth of the tear film is k λ/4, where k is an odd integer, as discussed above in relation to FIG. 2.

Figure 5A:
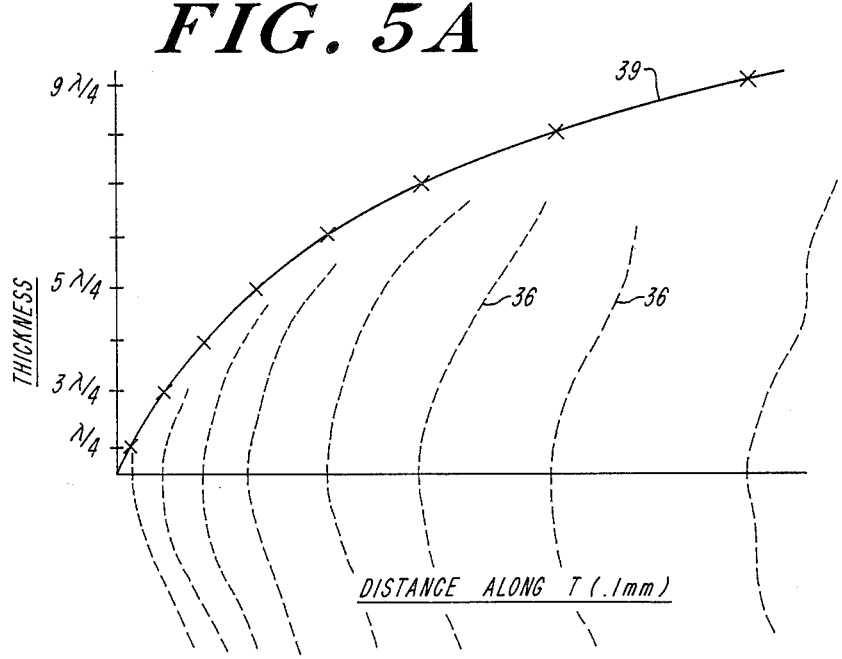
FIG. 5A is a graph of film thickness.

FIG. 5A shows a representative graph 39 of tear film thickness along a line T', such as line T of FIG. 5, imposed on a recorded interference pattern (shown in phantom). A dry edge is chosen as the origin. Each point at which line T' crosses a dark interference band is indicated by a transverse line marked on the horizontal axis. These coordinates may be directly ascertained by measurement of the filmed image, since the scale is known. Tear film thickness is indicated in increments of λ/2, starting at λ/4, along the vertical axis. Each successive dark band crossed by line T' indicates an increment or decrement of film thickness by λ/2. For purposes of this example, it is assumed that the bands adjacent to the edge are representative of increasing thickness. It will be seen that, with the T' and thickness axes calibrated in identical units, the slope of the tangent line to graph 39 is the tangent of the classical contact angle.

The field of view with the apparatus shown in FIG. 3, over which the focus of the image of the curved prelens film is sharp enough to include well-defined interference bands is approximately 4–6 mm diameter, and may be extended by appropriate optics. Thus the device of FIG. 3 provides a recorded image which is a topographic map of prelens tear film depth over a substantial portion of the lens. By themselves, the interference bands give only relative, and not absolute, film thickness information; the spacing of two dark bands gives a measure of the slope of the tear film depth between the two dark bands. In addition, certain patterns such as local occurrences of concentric closely spaced closed contours 38a, 38b may be recognized as local peaks or valleys of the fluid film. During recording of the frames 30, which is accomplished with a fixed camera at constant magnification, a millimeter rule is first placed in the object plane and photographed. Thus, absolute spacing of the bands shown in a frame 30 may be readily ascertained. Knowing the absolute spacing, the slope of the film at a point is determined as $\lambda/2$ divided by the band spacing. Thus, the band spacing approaching a dry edge of the film gives a direct numerical measure of the tangent of the contact angle.

When one observes a time sequence of frames 30, the bands 36a, 36b will be seen to move across the field, change contour, and disappear. Most commonly the "bull's eye" regions 38a, 38b will exhibit behavior indicative that they are dry spots of thickness t such that $0 \leq t < \lambda/4$. The bull's eye will first appear at some time after the subject blinks, and the rings of the bull's eye will migrate radially outward as the film further dries. When a spot D has been identified as dry by this criterion, and its position noted, the absolute tear film thickness distribution over the entire field may then be determined for each instant in time by merely correlating the interference bands, starting at a dry spot, in preceding frames 30. Thus for example the first dark ring about D indicates a contour of film thickness $t = \lambda/4$. That ring, followed through each preceding frame, is a contour indicating locations over the lens having the same film depth. The next contour out from the dry spot has a tear film thickness $\lambda/2$ greater.

Thus the invention includes a method, and the apparatus for performing the method, for the direct observation and computation of the actual tear film thickness distribution, at each instant in time, on a contact lens. In addition to film thickness, other measurements of different types may readily be defined and experimentally observed to determine both their appropriateness as criteria of wetting, and the correlation of such measure with conventional criteria.

By way of example, for a given lens material or treatment fluid, a measure such as the time interval until tear film breakup, or such as the average tear film thickness following blinking may be quickly ascertained. Dry spots may be correlated with deposits built up from previous drying cycles, and the efficacy of cleaners on, or the resistance of lens materials to, such deposits may be directly measured.

Figure 6:
FIG. 6 is a block diagram of a preferred apparatus.

Such measurements are performed in accordance with the presently preferred embodiment of the invention using the apparatus shown in FIG. 6. An interference pattern imaging and recording apparatus 40, such as that shown in FIG. 3 records a time sequence image of the interference pattern localized in the tear film. The film is placed in a film motion analyzer 50 which is used to develop output signals indicative of the time, x-position and y-position of features selected by an operator. A microprocessor 60 receives the output signals and, operating according to an operator selected program, calculates the desired measurement.

In the prototype embodiment the apparatus 40 recorded the images on 16 mm black and white movie film at 25 frames per second, so that sequential frames had time coordinates differing by 0.04 seconds. The analyzer 50 was a Film Motion Analyzer made by NAC of Japan and marketed in the United States by Instrumentation Marketing of Burbank, Calif. The basic elements of analyzer 50 include a screen onto which the film is projected, a coordinate grid overlaid on the screen, and a handpiece having cross-hairs and a selector button thereon the actuation of which causes the analyzer to output the frame number and the (x,y) coordinates of the point on the screen under the cross-hairs. The microprocessor 60 was an Apple computer, programmed to carry out basic processing and storage of the data from the analyzer 50, such as calculation of the film thickness gradient, plotting of the thickness distribution, or calculation of the film drying time. Such a system 40, 50, 60 permits the ready measurement of wetting characteristics of a lens worn by a user, enabling the direct experimental evaluation of materials, cleaners and conditions which were previously evaluated by theoretical projections.

Other measures of immediate clinical utility may be readily defined and reduced to elementary computer-implemented programs. For example, the drying half-time, defined as the time interval following blink until one-half of the lens area is dry, or the dry spot count, defined as the number of discrete dry spots formed before a fixed time following blink, may be ascertained.

The invention having been thus disclosed, diverse changes and variations in the apparatus and method will occur to those skilled in the art, and all such changes and modifications are intended to be within the scope of the invention, as set forth in the following claims.

What is claimed is:

1. A method of measuring the in vivo wetting quality of a contact lens worn by a subject, such method comprising the steps of
    supporting the subject's head so as to maintain the lens in a fixed location
    illuminating the pre-lens tear film with coherent light
    recording a time sequence image of the pattern of interference bands formed by specular reflectance of the light from the pre-lens film, and
    correlating the position of sequential recorded images of at least one interference band so as to obtain a measurement of said wetting quality.

2. The method of claim 1 wherein the step of correlating includes the step of determining the spacing between adjacent pairs of interference bands proximate to an edge of the film, and wherein the measured wetting quality is the contact angle.

3. The method of claim 1 wherein the step of correlating includes correlating the sequential motion of interference bands past a fixed position so as to identify the formation of a dry spot, and wherein the measured wetting quality is the time interval between the subject's blink and the onset of tear film break-up.

4. The method of claim 1, wherein the step of corrolating includes comparing local irregularities in the interference pattern at different locations on the lens to determine the existence of variations in wetting quality.

5. The method of claim 1 further including the step of treating the lens with a treatment fluid before performing said steps of recording and correlating.

6. The method of claim 5 wherein the step of correlating includes correlating so as to obtain a measurement of a said quality for a new lens, correlating so as to obtain a measurement of the same quality for a lens which has been worn for a known time interval, and comparing the two said measurements to develop a measurement of change in the said wetting quality.

7. A method of determining a wetting quality of a contact lens worn by a subject, such method comprising the steps of
    supporting the subject's head so as to determine a fixed location of the contact lens
    illuminating the pre-lens tear film with coherent light
    recording a time sequence image of the light specularly reflected by the tear film and determining the tear film thickness from the recorded time sequence image, said thickness at a particular time being indicative of the wetting quality.

8. Apparatus for the evaluation of an ophthalmic wetting characteristic, such wetting characteristic being a function of tear film thickness, wherein the apparatus comprises light means for directing incident light at a tear film on a subject's eye when the subject's head is supported in an observation position, and light collection means for collecting incident light which has been specularly reflected from, and for focusing an image of a surface region of, the tear film, for providing an image of the tear film, such image including a pattern of interference bands localized in said tear film surface region and formed by interference between incident light reflected from front and rear surfaces of said tear film so as to be indicative of tear film thickness, such light means and light collection means being arranged such that the light from the tear film collected and focused by the collection means consists substantially of light specularly reflected from the tear film whereby the interference bands are clearly defined throughout the region, thus enabling the wetting characteristic to be evaluated by determining the thickness over time.

9. Apparatus according to claim 8, wherein the light means directs coherent light at the eye, and wherein the light collection means includes a motion picture camera focused on the tear film and positioned to image the light from the light means specularly reflected from the tear film over said region.

10. Apparatus according to claim 9, wherein the light means directs substantially monochromatic light at the eye.

11. Apparatus according to claim 10, wherein the light means directs the light at the eye via converging optics having a central aperture, and the camera images the prelens tear film through said central aperture, whereby the camera images specularly reflected light from a region of the tear film.

12. Apparatus according to claim 8, wherein the light means includes a laser.

13. Apparatus for the evaluation of a wetting characteristic of a contact lens being worn by a subject, such wetting characteristic being a function of prelens tear film thickness, wherein the apparatus comprises means for supporting the subject's head so as to determine a fixed location of the contact lens, light means for directing coherent light at the lens, means for recording a time sequence image of the light specularly reflected from the prelens tear film, such image including a pattern of interference bands indicative of tear film thickness, and means operative on the time sequence recording of the image for determining time and space coordinates of the recorded interference bands, and for developing output signals indicative thereof whereby the wetting characteristic may be evaluated by determining the thickness.

14. Apparatus according to claim 13, further including computer means for computing the wetting characteristic from the said output signals.

15. Apparatus according to claim 14, wherein the means for determining coordinates determines coordinates of consecutive interference bands along line normal to a dry edge, and wherein the computer computes the contact angle.

16. Apparatus for the evaluation of a wetting characterstic of a contact lens being worn by a subject, such wetting characteristic being a function of prelens tear film thickness, wherein the apparatus comprises means for supporting the subject's head so as to determine a fixed location of the contact lens, light means for directing a scanning beam of coherent light at the lens via a first scanning mirror such that the light strikes a point x on the lens at an angle $\phi(x)$ to the normal, a second scanning mirror controlled to scan the point x in synchrony with the first mirror so as to receive light reflected from the point x at the angle $\phi(x)$, and camera means located to receive the light reflected from the second scanning mirror, for recording a time sequence image of the light specularly reflected from the prelens tear film, such image including a pattern of interference bands indicative of tear film thickness, whereby the wetting characteristic may be evaluated by determining the thickness.

* * * * *